(12) United States Patent
Daly

(10) Patent No.: US 6,723,115 B1
(45) Date of Patent: Apr. 20, 2004

(54) DISPOSABLE BODY PART WARMER AND METHOD OF USE

(75) Inventor: Paul C. Daly, Abington, MA (US)

(73) Assignee: Respironics Novametrix, Inc., Wallingford, CT (US)

( * ) Notice: Subject to any disclaimer, the term of this patent is extended or adjusted under 35 U.S.C. 154(b) by 0 days.

(21) Appl. No.: 09/671,387

(22) Filed: Sep. 27, 2000

(51) Int. Cl.$^7$ .................................................. A61F 7/00
(52) U.S. Cl. ........................ 607/111; 607/112; 607/108; 607/114
(58) Field of Search ................................ 607/111, 112, 607/114, 108, 96; 128/882; 602/65, 27, 14

(56) References Cited

U.S. PATENT DOCUMENTS

| | | | |
|---|---|---|---|
| 4,753,241 A | * | 6/1988 | Brannigan et al. .......... 156/210 |
| 4,872,442 A | | 10/1989 | Manker |
| 5,058,563 A | | 10/1991 | Manker |
| 5,143,048 A | | 9/1992 | Cheney, III |
| 5,184,613 A | | 2/1993 | Mintz |
| 5,305,733 A | | 4/1994 | Walters |
| 5,336,209 A | * | 8/1994 | Porzilli ........................ 128/888 |
| 5,358,140 A | * | 10/1994 | Pellegrino ................... 206/440 |
| 5,496,358 A | * | 3/1996 | Rosenwald .................. 126/204 |
| 5,791,334 A | | 8/1998 | Walters |
| 5,800,492 A | | 9/1998 | Manker |
| 5,915,461 A | | 6/1999 | Tanhehco |
| 6,440,159 B1 | * | 8/2002 | Edwards et al. ............ 607/108 |

OTHER PUBLICATIONS

Barker et al., *Capillary Blood Sampling: Should the Heel Be Warmed?*, Dept. of Neonatal Medicine and Surgery, Oct. 20, 1995, 2 pp.
Shah V., *Venepuncture Versus Heel Lance for Blood Sampling in Term Neonates*, Mount Sinai Hospital, Canada, Feb. 22, 1999, 11 pp.

* cited by examiner

*Primary Examiner*—Roy D. Gibson
(74) *Attorney, Agent, or Firm*—Michael W. Haas

(57) ABSTRACT

An apparatus for warming a portion of a human body, such as a foot of a neonatal infant, comprising an elongated, flexible pouch defining an internal chamber containing a selecting initiable heat generating material, the pouch including a first relatively longer segment and a second relatively shorter segment joined along a narrower neck region. The two segments are independently securable to, for example, the foot of an infant, the longer first segment being secured to the bottom of the foot and extending to the heel and the shorter segment extending upwardly from the heel. Independent securement may be effected by a strap secured to and extending transversely from each segment and having adhesive at a distal end thereof, one strap being wrapped over the instep of the infant to secure the larger segment and the other strap being wrapped forwardly about the ankle, the distal ends of both straps being adhered to their respect segments. A portion of each strap may be perforated to facilitate severance thereof and removal of the pouch from the patient after use.

20 Claims, 2 Drawing Sheets

DISPOSABLE BODY PART WARMER AND METHOD OF USE

BACKGROUND OF THE INVENTION

1. Field of the Invention

This invention relates generally to an apparatus for warming a site on a body part of a human in preparation for a medical procedure. More specifically, the invention relates to a disposable apparatus for warming the heel or foot of a newborn prior to lancing thereof to obtain a blood sample.

2. State of the Art

Hospitals perform numerous blood tests on newborns, generally termed "neonates", being defined as infants less than one month old. Because of the difficulty and danger of venepuncture in newborns, a preferred method of collecting a blood sample from a newborn is to lance or puncture the heel to a relatively shallow depth, on the order of 2 to 4 mm. This procedure is commonly termed a "heel stick". However, the heel stick skin puncture does not cause the blood to flow freely. Thus, the clinician may be tempted to squeeze the heel or perform a second stick to obtain a better sample. While application of minimal pressure to the puncture site may be tolerated, "milking", or massaging, the puncture site can cause hemolysis and contaminates the resulting blood sample with interstitial and intercellular fluid. Similarly, squeezing the heel causes bruising, evidencing hemorrhaging and creating fibrin deposits, both of which compromise the affected area of the heel for resampling at a later time.

Heel punctures in newborns may result in Calcaneal Osteomyelitis, a serious complication, and thus minimizing the number of skin punctures has been deemed imperative by practitioners in the field. In hospitals, newborns are by far the most frequently tested patients, with blood tests being repeated periodically in an average of over 79% of cases. The repetition percentage rises to 98% when blood gases must be monitored. Risks of infection as well as cartilage damage associated with repeated sampling could be decreased by reducing the number of skin punctures required to collect an adequate sample.

It is known that warming the skin in an area to be punctured increases capillary action by dilating the blood vessels and consequently increases the rate of blood flow to the target area. Therefore, a newborn's heel is typically warmed prior to a heel stick to increase the ease with which a blood sample is collected. The CPCC unanimously recommends warming of the site prior to puncture and, when collection of blood gases is the object of the procedure, have deemed prewarming to be "essential". The National Committee for Clinical Laboratory Standards specifically lists warming of the puncture site as part of the skin puncture procedure, as does the Handbook of Phlebotomy. Hospitals throughout the United States almost universally practice prewarming of an intended puncture site when dealing with neonatal infants.

Various warming devices in the form of disposable heat packs usable to warm an infant's heel are known in the art. For example, see U.S. Pat. No. 5,143,048 to Cheney, U.S. Pat. No. 5,184,613 to Mintz, U.S. Pat. No. 5,305,733 to Walters and U.S. Pat. No. 5,800,492 to Manker. The Mintz device is formed in a symmetrical, wide, hourglass shape to facilitate wrapping of one portion of the pack about the leg and the otherabout the foot of the patient and to completely encircle both the foot and lower leg. The symmetrical design is also purported to make the device easier to apply, there being purportedly no "wrong way" to position it. However, the Mintz device does not concentrate heat in the area to be prewarmed and its symmetrical shape and great width renders it unduly bulky, difficult to apply, uncomfortable for the infant and susceptible to loosening on an active infant.

Thus, it would be advantageous to provide a disposable heel warmer of a design which localizes heat in the target area for a skin puncture, easily conforms to the foot, may be securely affixed thereto, and easily removed therefrom for performance of a skin puncture after prewarming.

BRIEF SUMMARY OF THE INVENTION

The present invention comprises a disposable warming device, asymmetrically longitudinally configured for ease of application to, conformance to, and subsequent removal from, the foot of a human patient, typically a neonatal infant.

A warming device according to one embodiment of the present invention includes an elongated pouch containing a selectively initiable heat source therein and comprising first and second segments. The two segments are in communication within the pouch through a neck region of reduced lateral width defined by notches extending laterally inwardly from sidewalls of the first and second segments. The first segment is relatively longer than the second segment, and each segment has associated therewith structure for independently securing it to a body portion of a human.

In one embodiment, the structure for independently securing the pouch segments to the body portion comprises two straps, each extending transversely to a longitudinal axis of the pouch, secured to a segment by a proximal portion of the strap and including an adhesive area thereon at a distal portion thereof, a medial portion of each strap being adhesive-free. Each strap may optionally include a perforation line extending transversely thereacross to facilitate removal of the warming device after use. The warming device pouch may be formed of film of polymer or other suitable material folded upon itself and subsequently heat sealed about three sides thereof to contain the heat source therein, the fourth side comprising the fold line. Alternatively, the warming device pouch may be formed of two superimposed film segments and heat sealed about its entire periphery.

Also disclosed is a method of warming the heel of an infant comprising providing a warming device comprising an elongated pouch having a longitudinal axis, placing a first, relatively longer segment of the pouch under a foot of an infant to the heel thereof and placing a second, relatively shorter segment of the pouch over the ankle of the foot by folding the pouch along a line extending substantially between notched areas on opposing sides of the pouch, and separately securing the first segment at least about a bottom and sides of the foot and the second segment about the ankle.

While the present invention has utility as a heel warmer for newborns, it may be used in for older children and adults as well. The present invention is believed to have specific utility for geriatric patients, whose circulatory systems are often impaired. The present invention may be fabricated in a larger size, as necessary or desirable. Further, although the present invention is described herein for use on the heel of a patient, it will be appreciated that the present invention may be used to warm any body part, especially prior to initiating an IV or drawing blood.

DETAILED DESCRIPTION OF THE INVENTION

Figure 1:
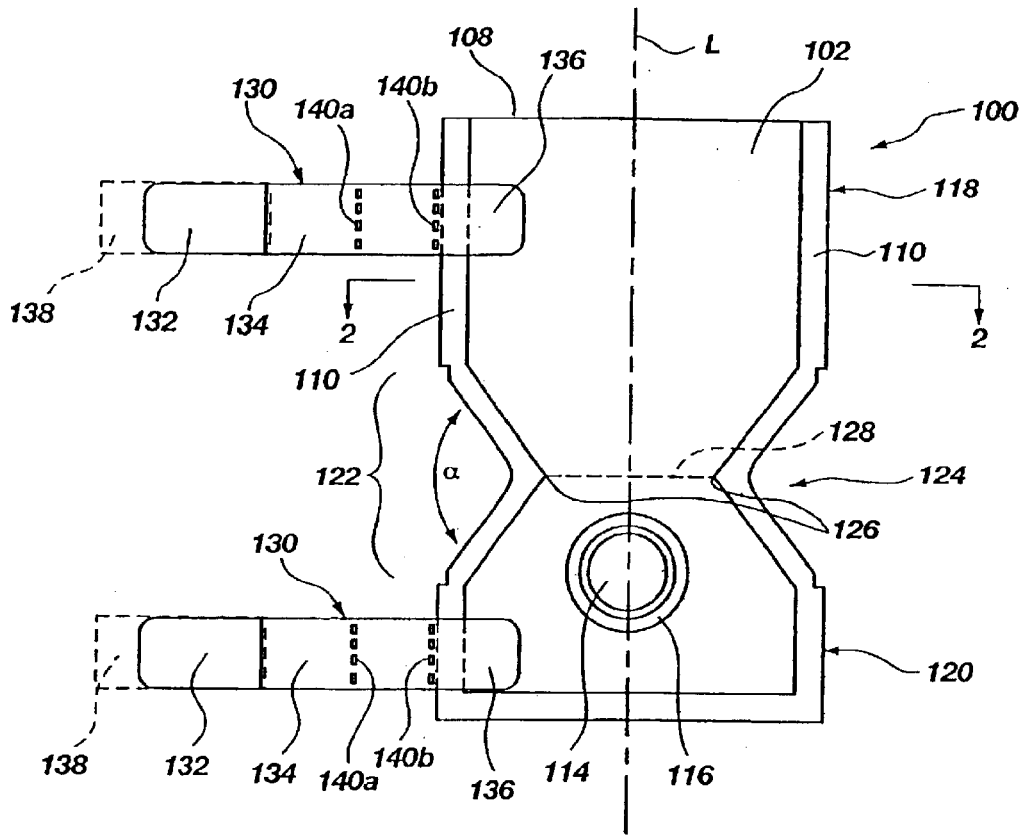
FIG. 1 is a frontal elevation of one embodiment of the warming device of the present invention.
Figure 2:
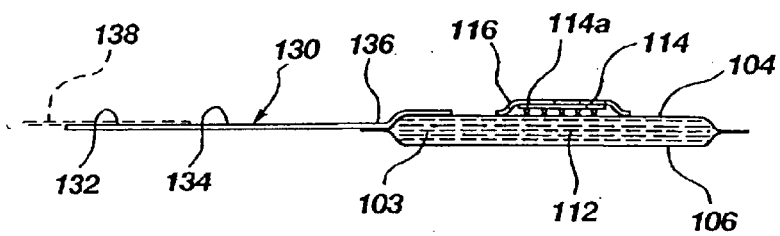
FIG. 2 is a side partial sectional elevation of the warming device of FIG. 1.

FIG. 1 depicts a warming device 100 according to one embodiment of the present invention. Warming device 100 comprises a flexible, elongated, substantially rectangular pouch 102 formed of a thin-walled polymer. One suitable material for the pouch 102 is 0.002 inch thick, clear polyethylene. Other suitable materials include silicones, urethanes, rubbers, vinyls, vinyl-coated fabric and nylon polylaminates, with wall thicknesses ranging from about 1 mil (0.001 inch) to about ten mils (0.010 inch). As shown, pouch 102 is formed by mutually superimposing two identical pouch sides 104 and 106 along a fold line 108 transverse to longitudinal axis L of pouch 102, and heat sealing together adjacent, superimposed edges of the two pouch sides as known in the art to form an internal chamber 103. Heat sealed border 110 extends about the edges of pouch 102 other than that defined by fold line 108 and is completed after chamber 103 of pouch 102 is filled with a supercooled salt solution 112 which, when activated, crystallizes and releases heat. It is also contemplated, as previously noted, that two separate film segments may be superimposed and bonded about the entire mutual peripheries thereof to form pouch 102 with internal chamber 103. Heat sealing may be effected by any technique known in the art including, without limitation, resistance heating and laser welding.

Suitable supercooled salt solutions include supercooled sodium acetate, lead acetate, calcium nitrate tetrahydrate, sodium polyphosphate and sodium thiosulfate. Food grade sodium acetate with water and thickeners is a currently preferred formulation for solution 112, all of the components being generally harmless to humans. The formulation is effected to achieve an end temperature of about 105° F. (41° C.). Initiation of crystallization is achieved by exposing the solution 112 to even a minute quantity of air, which may be effected by perforating a wall of pouch 112. As shown, a substantially rigid metal disc 114 having tines or prongs 114a projecting transversely therefrom may be placed adjacent an exterior surface of pouch 102 and covered, for example, with a flexible sealing element 116 to retain disc 114 on pouch 102 prior to use and to prevent any possible leakage of solution 112. A more complete explanation of the use of supercooled salt solutions, of techniques and structures for initiating crystallization of same to release heat and of formulating solutions to regulate heat released during crystallization thereof are disclosed in U.S. Pat. No. 5,305,733 referenced above, the disclosure of which patent is hereby incorporated herein by this reference.

As depicted in FIG. 1, warming device 100 is elongated and is asymmetrical longitudinally, including a first relatively longer segment 118 and a second relatively shorter segment 120 which communicate through interposed, narrower neck region 122 defined by opposing, V-shaped notches 124 opening at angles α which may range from about 30° to about 150°. Angle α preferably lies with a range of between about 90° and about 100°. Smaller angles α may be employed, for example, if greater overlap of segments 118 and 120 is desired when warming device 100 is applied to a body part as hereinafter described. Larger angles α may be employed where, for example, segments 118 and 120 are to be folded into substantial mutual superimposition, as about the hand or forefoot of a patient. A fold line 128 is defined substantially between apices 126 of notches 124, and fold line 128 may be used as a guide in some instances for placement of warming device 100. The outer edges of border 110 of pouch 102 are rounded adjacent and laterally outboard from the apices 126, and border 110 is relatively narrower within notches 124 to facilitate folding of one segment 118, 120 of pouch 102 transversely relatively to the other segment 118, 120.

Each segment, 118, 120 has affixed thereto a strap 130 oriented substantially transversely to longitudinal axis L, each strap 130 preferably comprising a paper tape of sufficient strength for affixing warming device 100 securely to a body part and having a distal end portion 132 carrying a transfer contact adhesive. A medial portion 134 of each tape 130 is adhesive-free, and a proximal portion 136 of each tape 130 is affixed to the exterior surface 138 of one of segments 118 and 120 by an adhesive or other bonding technique. Prior to use, the adhesive-coated distal portions 132 of tapes 130 are covered with removable tabs 138. As tapes 130 are relatively robust to ensure continued affixation of warming device 100 to a patient's body part after application thereto, medial portions 134 of tapes 130 may also be optionally perforated transversely to their direction of elongation as shown at exemplary alternative locations 140a and 140b to facilitate severance of tapes 130 and removal of warming device 100 after use. Location 140b is currently preferred, as the proximity of the perforations at location 140b to border 110 facilitates tearing by twisting one edge of the tape 130 upwardly at or adjacent a line of perforations.

Other techniques may be used to affix distal portions 132 of tapes 130 to the exterior surface of pouch 102. For example, a hook and loop fastening system such as that marketed under the Velcro® brand, may be employed. Further, tapes or straps 130 may be formed integrally with pouch 102, from the same sheet of material.

In use, pouch 102 is pinched over disc 114 to puncture the wall of pouch 102 with tines 114a and initiate crystallization of solution 112 through exposure to air trapped under flexible sealing element 116. Optionally, pouch 102 is kneaded to soften the solution throughout pouch 102 and accelerate crystallization of solution 112 throughout pouch 102. As solution 112 crystallizes, pouch temperature increases from ambient to about the aforementioned 105° F. (41° C.) and remains at about such temperature for three or four minutes. Pouch 102 is placed with fold line 128 (which may be marked on pouch 102 for clarity and ease of use) at the rear of the infant's heel, longer first segment 118 extending under the foot and shorter second segment 120 extending upwardly at the rear of the foot behind the ankle. Tape 130 associated with longer, first segment 118 is then extended over the instep of the foot and adhered by its adhesive carrying distal portion 132 to the exterior of first segment 118 of pouch 102 on the opposing side of the foot. Similarly, tape 130 associated with shorter, second segment 120 is extended forwardly about the ankle and adhered by its adhesive carrying distal portion 132 to the exterior of second segment 120 of pouch 102 on the opposing side of the ankle. Thus, both first segment 118 and second segment 120 are independently secured to the foot. Removable tabs 138 preferably remain over the adhesive on distal portions 132 of tapes 130 until immediately prior to their adherence to the respective, desired portions of pouch 102 to prevent inadvertent adherence to the infant's skin or an undesired portion of pouch 102. The adhesive employed on distal portions 132 of tapes 130 may be formulated so as to securely adhere in a non-removable fashion to pouch 102, or may be formulated so as to permit repeated lifting of distal portions 132 from pouch 102 and re-application thereto as required or desired to adjust the fit of warming device 100.

Figure 3:
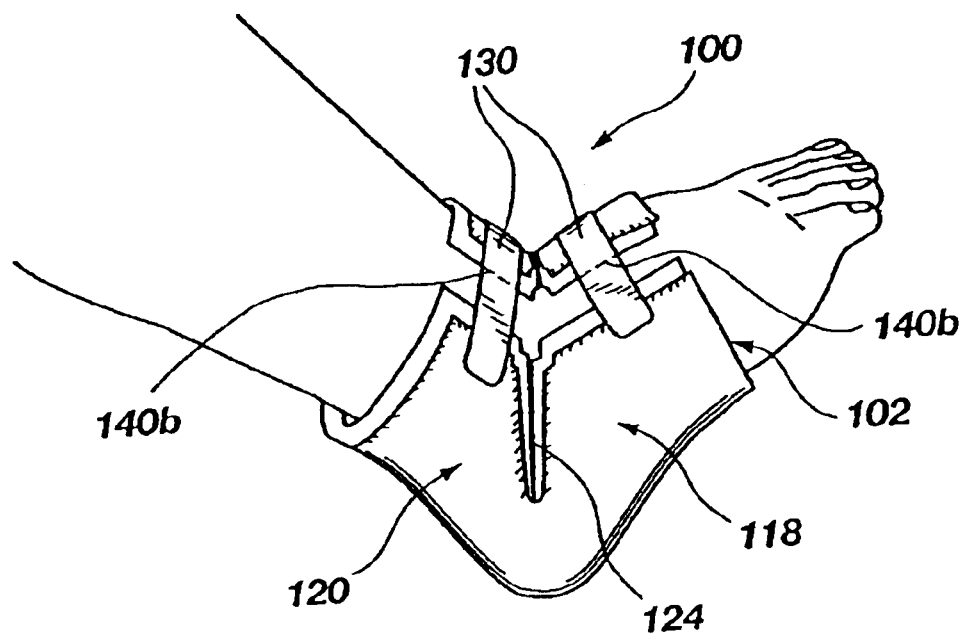
FIG. 3 is a perspective view of the warming device of the present invention secured over an infant's foot.

FIG. 3 depicts warming device 100 affixed to the foot of an infant, with pouch 102 oriented so that first segment 118 cups the bottom of the foot, extending up the sides thereof so that tape 130 associated with segment 118 fits snugly under the arch and over the instep. Second segment 118, in combination with tape 130 associated therewith, encircles the ankle. It should be noted that notches 124 have collapsed or closed when warming device 100 is properly placed, enhancing heat retention proximate the heel of the infant.

Exemplary dimensions for a warming device 100 for use with neonatal infants may be described with respect to FIG. 1. The length of pouch 102 may be about 5.5 inches (or about 5.25 inches excluding heat seal border 110 at the outer end of second segment 120), while the width, which is substantially constant but for notches 124, maybe about 3.5 inches (or about three inches excluding heat seal border 110 on each side of pouch 102). Each tape 130 may extend about 2.75 inches from the side of pouch 102, measured from the outer edge of heat seal border 110, with adhesive on distal portions 132 for a distance of about an inch from the distal ends. One tape 130 is disposed about six-tenths of an inch from an outer end of first segment 118, while the other tape 130 is disposed just inside of heat seal border 110 proximate an outer end of second segment 120. The mouths of notches 124 are about two inches wide, and notches 124 are about one inch deep, measured transverse to longitudinal axis L and between apices 126 and the outer edge of heat seal border 110 along first and second segments 118 and 120. The length of first segment 118 is about 3.25 inches to fold line 128, while the length of second segment 120 is about two inches to fold line 128 excluding heat seal border 110 and about 3.25 inches including same. The above listed dimensions are provided as an illustration only. Those skilled in the art will appreciate that the dimensions may be modified to ensure a better fit on a patient, such as an adult, if required.

While the present invention has been described and illustrated in terms of a specific illustrated embodiment, those of ordinary skill in the art will understand and appreciate that it is not so limited. Additions to, deletions from and modifications to the illustrated embodiment may be effected without departing from the scope of the invention as defined by the claims.

What is claimed is:

1. A warming device for application to a portion of a human body, comprising:
   (a) an elongated pouch defining an internal chamber, wherein the pouch comprises:
      (1) a first segment having a first size,
      (2) a second segment having a second size, and
      (3) a neck region of lessor lateral extent than either the first or second segments communicating the first segment with the second segment, wherein the first size of the first segment is substantially larger than the second size of the second segment;
   (b) a material selectively initiable to generate heat disposed within the internal chamber; and
   (c) a structure adapted to secure the first segment and the second segment on the portion of the human body.

2. The warming device of claim 1, wherein the neck region is defined between laterally opposing, outwardly facing notches on opposing sides of the pouch.

3. The warming device of claim 2, wherein each of the notches is V-shaped and spans an included angle of between about 30° and about 150°.

4. The warming device of claim 3, wherein each of the notches spans an included angle of between about 90° and about 100°.

5. The warming device of claim 1, wherein the pouch is formed as two superimposed pouch sides heat sealed about at least a portion of a periphery of the pouch with the material selectively initiable to generate heat disposed within the internal chamber.

6. The warming device of claim 5, wherein the at least a portion of the periphery of the pouch comprises a border having a width, and a border width within the neck region is relatively narrower than a border width outside and proximate the neck region.

7. The warming device of claim 6, wherein the neck region is defined between laterally opposing, outwardly facing, V-shaped notches on opposing sides of the pouch, each notch spans an included angle of between about 30° and about 150°, and an outer edge of the border adjacent each notch apex is arcuate.

8. The warming device of claim 7, wherein each of the notches spans an included angle of between about 90° and about 100°.

9. The warming device of claim 1, wherein the structure for independently securing the first segment and the second segment on the portion of the human body comprises first and second straps, one strap being secured at a proximal end thereof to each of the first and second segments and extending laterally therefrom substantially transversely to a longitudinal axis of the pouch.

10. The warming device of claim 9, further comprising an adhesive disposed on a distal portion of each of the straps.

11. The warming device of claim 10, wherein a medial portion of at least one of the straps is devoid of adhesive.

12. The warming device of claim 10, wherein a portion of at least one of the straps is perforated.

13. The warming device of claim 1, wherein the pouch is formed of a polymer and the material selectively initiable to generate heat disposed within the internal chamber comprises a supercooled salt solution.

14. The warming device of claim 13, wherein the polymer comprises polyethylene and the supercooled salt solution comprises sodium acetate.

15. A method of warming a heel of an infant, comprising:
   providing a warming device comprising a flexible, elongated pouch including a first segment having a first size, a second segment having a second size, and a neck region of reduced width joining the first and second segments, wherein the first segment, the second segment, and the neck region define a continuous internal chamber containing a selectively initiable heat generating material, and wherein the first size of the first segment is substantially larger than the second size of the second segment;
   initiating the heat generating material;
   securing the first segment of the pouch in position at least along an underside and sides of an infant's foot with the neck region at a rear of a heel thereof; and
   securing the second segment of the pouch in position at least extending upwardly from the rear of the heel and forwardly about at least a portion of an ankle of the infant.

16. The method of claim 15, wherein independently securing the first segment is effected by extending a strap secured to one side of the first segment over an instep of the foot and securing a distal end of the strap to the first segment.

17. The method of claim 16, wherein independently securing the second segment is effected by extending a second strap secured to one side of the second segment forwardly about the ankle and securing a distal end of the second strap to the second segment.

18. The method of claim 15, wherein independently securing the second segment is effected by extending a strap secured to one side of the second segment forwardly about the ankle and securing a distal end of the strap to the second segment.

19. The method of claim 17, further comprising configuring the neck region with two opposed, outwardly facing, V-shaped notches, and mutually folding the first and second segments of the elongated pouch along a fold line extending between apices of the notches to at least substantially close the notches when placing the warming device on the infant's foot and place the first and second segments in close mutual proximity adjacent the heel thereof.

20. The method of claim 15, further comprising removing the warming device from the heel of the infant's foot by severing at least one portion of the warming device at a preselected location.

* * * * *